(12) United States Patent
Lee et al.

(10) Patent No.: US 12,409,270 B2
(45) Date of Patent: Sep. 9, 2025

(54) OPTIMIZING EMBEDDED FORMULATIONS FOR DRUG DELIVERY

(71) Applicant: Insulet Corporation, Acton, MA (US)

(72) Inventors: Joon Bok Lee, Acton, MA (US); Yibin Zheng, Hartland, WI (US); Jason O'Connor, Acton, MA (US); Ashutosh Zade, San Diego, CA (US)

(73) Assignee: INSULET CORPORATION, Acton, MA (US)

(*) Notice: Subject to any disclaimer, the term of this patent is extended or adjusted under 35 U.S.C. 154(b) by 663 days.

(21) Appl. No.: 17/752,236

(22) Filed: May 24, 2022

(65) Prior Publication Data

US 2023/0166034 A1 Jun. 1, 2023

Related U.S. Application Data

(63) Continuation of application No. 17/539,270, filed on Dec. 1, 2021, now Pat. No. 11,439,754.

(51) Int. Cl.
| | | |
|---|---|---|
| A61M 5/172 | (2006.01) | |
| A61M 5/142 | (2006.01) | |
| G16H 20/17 | (2018.01) | |

(52) U.S. Cl.
CPC ...... *A61M 5/1723* (2013.01); *A61M 5/14244* (2013.01); *G16H 20/17* (2018.01); *A61M 2005/14208* (2013.01); *A61M 2230/201* (2013.01)

(58) Field of Classification Search
None
See application file for complete search history.

(56) References Cited

U.S. PATENT DOCUMENTS

| | | |
|---|---|---|
| 5,007,286 A | 4/1991 | Malcolm et al. |
| 6,544,212 B2* | 4/2003 | Galley ............... A61B 5/7275 |
| | | 604/504 |
| 6,553,841 B1 | 4/2003 | Blouch |
| 10,332,632 B2 | 6/2019 | Duke et al. |
| 10,737,024 B2 | 8/2020 | Schmid |
| 10,881,792 B2* | 1/2021 | Mazlish ............ A61B 5/14532 |
| 10,987,468 B2 | 4/2021 | Mazlish et al. |

(Continued)

FOREIGN PATENT DOCUMENTS

| | | |
|---|---|---|
| AU | 2015200834 A1 | 3/2015 |
| EP | 2897071 B1 | 5/2019 |

(Continued)

OTHER PUBLICATIONS

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

(Continued)

*Primary Examiner* — Manuel A Mendez
(74) *Attorney, Agent, or Firm* — Goodwin Procter LLP (57) ABSTRACT

Disclosed herein is a method for execution by a drug delivery device for determining an optimal dose of a liquid drug for current cycle of a medication delivery algorithm, the method utilizing a stepwise evaluation of a model and a cost function across a coarse search space consisting of coarse discrete quantities of the drug and a refined search space consisting of refined discrete quantities of the drug.

20 Claims, 3 Drawing Sheets

(56) References Cited

U.S. PATENT DOCUMENTS

| | | |
|---|---|---|
| 2014/0146202 A1 | 5/2014 | Boss et al. |
| 2015/0120317 A1 | 4/2015 | Mayou et al. |
| 2015/0134265 A1 | 5/2015 | Kohlbrecher et al. |
| 2016/0038673 A1 | 2/2016 | Morales |
| 2016/0354543 A1 | 12/2016 | Cinar et al. |
| 2018/0200434 A1 | 7/2018 | Mazlish et al. |
| 2020/0342974 A1 | 10/2020 | Chen et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| JP | 2019525276 A | 9/2019 |
| WO | 2005082436 A1 | 9/2005 |
| WO | 2007078937 A1 | 7/2007 |
| WO | 2010053702 A1 | 5/2010 |
| WO | 2010132077 A1 | 11/2010 |
| WO | 2010138848 A1 | 12/2010 |
| WO | 2015187366 A1 | 12/2015 |
| WO | 2016004088 A1 | 1/2016 |
| WO | 2017091624 A1 | 6/2017 |
| WO | 2019213493 A1 | 11/2019 |
| WO | 2021011738 A1 | 1/2021 |
| WO | 2021026004 A1 | 2/2021 |
| WO | 2021163326 A1 | 8/2021 |

OTHER PUBLICATIONS

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Medication Bar Code System Implementation Planning Section II: Building the Case for Automated Identification of Medications, Aug. 2013.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand col. line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php? title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, KP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

International Search Report and Written Opinion for International Patent Application No. PCT/US2022/051534, mailed Apr. 4, 2023, 10 pages.

\* cited by examiner

OPTIMIZING EMBEDDED FORMULATIONS FOR DRUG DELIVERY

RELATED APPLICATIONS

This application is a continuation of U.S. patent application Ser. No. 17/539,270, filed Dec. 1, 2021, the contents of which are incorporated herein by reference in their entirety.

BACKGROUND

Figure 2:
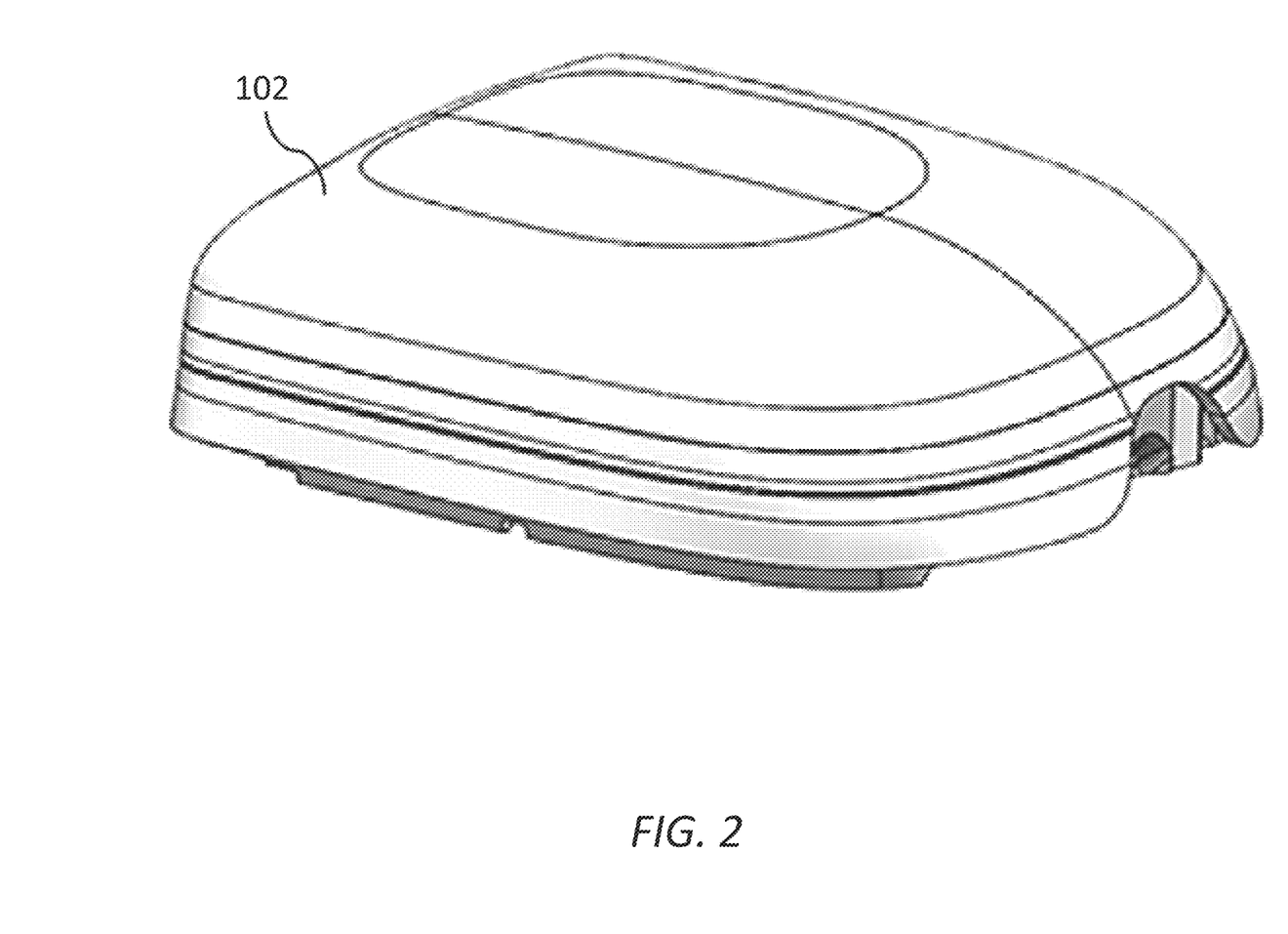
FIG. 2 is a depiction of a prior art wearable drug delivery device of the type in which the invention disclosed herein would be used.

Many conventional automatic drug delivery systems are well known, including, for example, wearable drug delivery devices of the type shown in FIG. 2. The drug delivery device 102 can be designed to deliver any type of liquid drug to a user. In specific embodiments, the drug delivery device 102 can be, for example, an OmniPod® drug delivery device manufactured by Insulet Corporation of Acton, Massachusetts. The drug delivery device 102 can be a drug delivery device such as those described in U.S. Pat. Nos. 7,303,549, 7,137,964, or U.S. Pat. No. 6,740,059, each of which is incorporated herein by reference in its entirety.

Wearable drug delivery devices 102 are typically configured with a processor and memory and are often powered by an internal battery or power harvesting device having limited amount of power available for powering the processor and memory. Further, because of the size of the device, the processing capability and memory for storage of software algorithms may also be limited. Due to these limitations, wearable drug delivery devices do not have an onboard medication delivery algorithm that determines, through a series of calculations based on feedback from sensors and other information, the timing and quantity of the liquid drug to be delivered to the user. Such medication delivery applications are typically found on a remote device, such as a remote personal diabetes manager (PDM) or a smartphone, for example, either of which being configured to transmit drug delivery instructions.

The medication delivery algorithm may use an optimization algorithm to periodically calculate the quantity of the liquid drug to be delivered to the user. For example, the medical delivery algorithm may operate, in one embodiment, on a 5-minute cycle. The optimization algorithm may utilize a mathematical glucose model and may minimize a cost function to determine the appropriate quantities of the liquid drug to be delivered. Such optimization algorithms often require a series of complex calculations with high computational and power consumption costs, making them difficult to implement in applications where only a low-power, efficient processing capability is available, such as in embedded applications. This is particularly important when it is desired to implement such optimization algorithms in disposable, small-scale electronics, such as a wearable drug delivery device 102.

Therefore, it would be desirable to provide a method to reduce the computational costs and power consumption for performing the optimization algorithm, to enable the medication delivery algorithm to reside onboard a wearable drug delivery device 102, and to enhance the life of the wearable drug delivery device 102 and the speed at which proper drug dosages can be calculated for delivery of the drug to the user or wearer of the wearable drug delivery device 102.

Definitions

As used herein, the term "liquid drug" should be interpreted to include any drug in liquid form capable of being administered by a drug delivery device via a subcutaneous cannula, including, for example, insulin, GLP-1, pramlintide, morphine, blood pressure medicines, chemotherapy drugs, fertility drugs or the like or co-formulations of two or more of GLP-1, pramlintide, and insulin.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In certain embedded, medical implementations, such as in a wearable drug delivery device 102, the precise solution to the optimization problem may not be required. This is largely due the fact that the difference in calculated doses for each cycle between an exact solution to the optimization problem and a close solution to the optimization problem may be below the minimum drug delivery resolution of the wearable drug delivery device 102. For example, in certain embodiments, the resolution of the delivery of the liquid drug may be limited to a fixed amount (e.g., 0.05 U, or 0.0005 mL). That is, the wearable drug delivery device 102 may only be capable of delivering the liquid drug in particular, discrete amounts. Therefore, an exact solution to the optimization problem providing a recommended dose that falls in between the particular, discrete amounts cannot be delivered, and, therefore, an approximation of the solution to the optimization problem is acceptable. Further, the differences between the calculated dose and the dose that the wearable drug delivery device 102 is capable of delivering to the user may not result in significant differences in the clinical outcome for the user. In some embodiments, the medication delivery algorithm may round the delivery to the nearest discrete amount capable of being delivered and add or subtract any differences to or from the calculated dose during the next cycle.

Therefore, the computational cost of executing the optimization algorithm can be greatly reduced (by 99%+) with a simple implementation of the optimization algorithm that allows the system to reach a solution that need not be accurate to the smallest decimal points but is sufficiently close so as to not impact the user's therapy.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

This disclosure presents various systems, components and methods for calculating a quantity of a liquid drug to be delivered to a user during a current execution cycle of a medication delivery algorithm. The embodiments described herein provide one or more advantages over conventional, prior art systems, components and methods, namely, a savings in power consumption and lower required processing power due to a simplified computational model used to solve the optimization problem.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1:
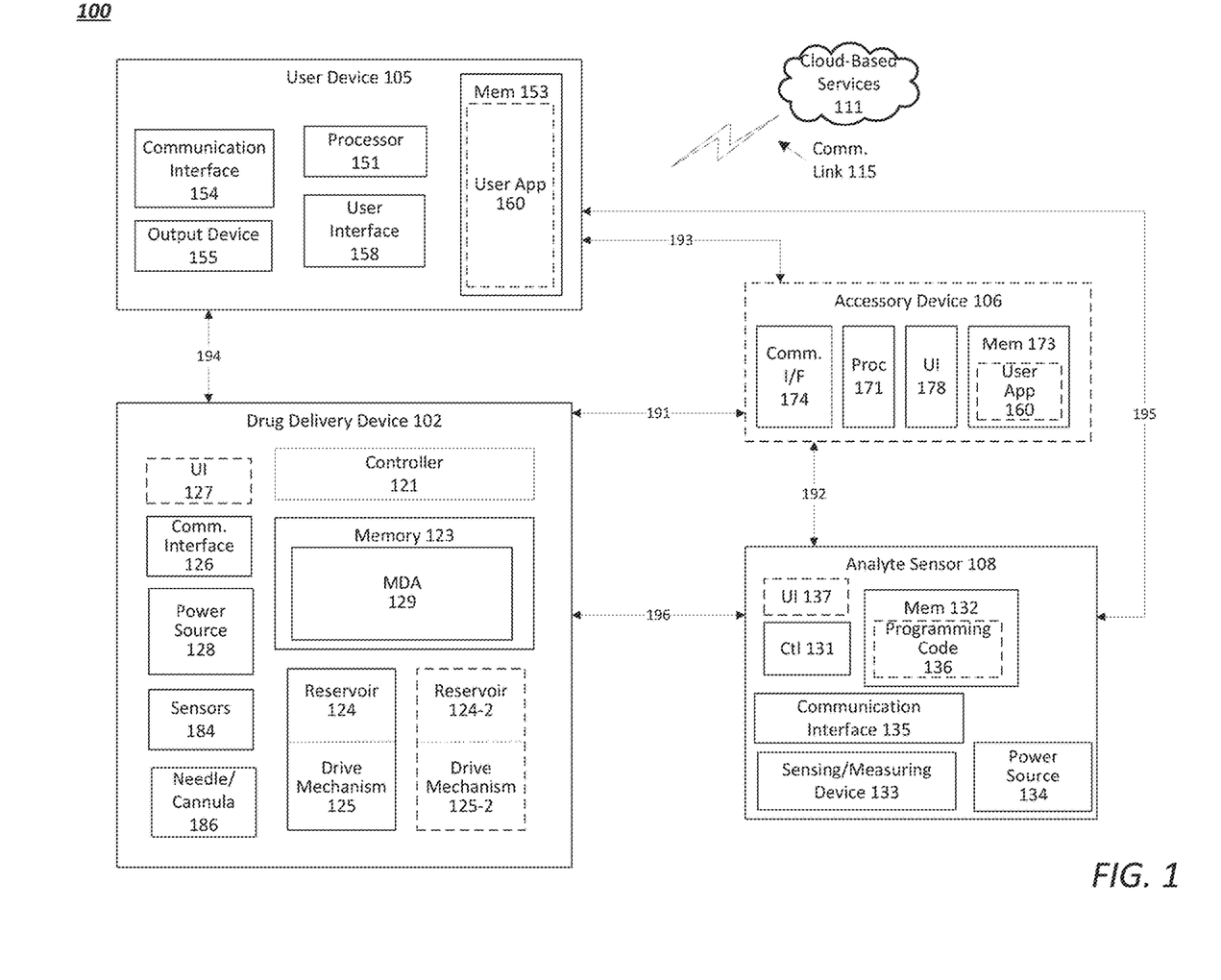
FIG. 1 illustrates a functional block diagram of an exemplary system suitable for implementing the systems and methods disclosed herein.

FIG. 1 illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, or the like, which may communicate with the other components of system 100 via either a wired or wireless communication links 191-193.

User Device

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like, as discussed below. The user device 105 may be used to program, adjust settings, and/or control operation of drug delivery device 102 and/or the analyte sensor 108 as well as the optional smart accessory device 106.

The processor 151 may also be configured to execute programming code stored in device memory 153, such as the user app 160. The user app 160 may be a computer application that is operable to deliver a drug based on information received from the analyte sensor 108, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an AP application, the processor 151 is also configured to execute a diabetes treatment plan (which may be stored in a memory) that is managed by user app 160. In addition to the functions mentioned above, when user app 160 is an AP application, it may provide further functionality to determine a carbohydrate-compensation dosage, a correction bolus dosage and determine a basal dosage according to a diabetes treatment plan. In addition, as an AP application, user app 160 provides functionality to output signals to the drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123 onboard the drug delivery device (and in exemplary embodiments, a wearable drug delivery device). Alternatively, controller 121 may act to control reservoir 124 and drive mechanism 125 based on signals received from user app 160 executing on a user device 105 and communicated to drug delivery device 102 via communication link 194. Drive mechanism 125 operates to longitudinally translate a plunger through the reservoir, such as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a micro-display, a microphone, an accelerometer for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface 186 may be, for example, a needle or cannula for delivering the drug into the body of the user (which may be done subcutaneously, intraperitoneally, or intravenously). Drug delivery device 102 may further include a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place.

In one embodiment, drug delivery device 102 includes a communication interface 126, which may be a transceiver that operates according to one or more radio-frequency protocols, such as Bluetooth®, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, IOB, insulin remaining, and the like, and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

Drug delivery device 102 may be a wearable device and may be attached to the body of a user at an attachment location and may deliver any therapeutic agent, including any drug or medicine, such as insulin or the like, to a user at or around the attachment location. A surface of drug delivery device 102 may include an adhesive to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from the respective external devices as well as implementing delivery of a drug to the user according to a diabetes treatment plan or other drug delivery regimen.

Accessory Device

Optional accessory device 107 may be a wearable smart device, for example, a smart watch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be a continuous glucose monitor (CGM) configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from drug delivery device 102, in various embodiments, the analyte sensor 108 and drug delivery device 102 may be incorporated into the same unit. That is, in various examples, the analyte sensor 108 may be a part of and integral with drug delivery device 102 and contained within the same housing as drug delivery device 102 or in a housing attachable to the housing of drug delivery device 102 or otherwise adjacent thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from cloud-based services 111. Services provided by cloud-based services 111 may include data storage that stores personal or anonymized data, such as blood glucose measurement values, historical IOB or TDI, prior carbohydrate-compensation dosage, and other forms of data. In addition, the cloud-based services 111 may process anonymized data from multiple users to provide generalized information related to TDI, insulin sensitivity, IOB and the like. The communication link 115 that couples the cloud-based services 111 to the respective devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 126, 135, 154 and 174.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may configured to operate in a manual mode in which user app 160 will deliver insulin at programmed basal rates and bolus amounts with the option to set basal profiles for different times of day or temporary basal profiles. The controller 121 will also have the ability to function as a sensor-augmented pump in manual mode, using sensor glucose data provided by the analyte sensor 108 to populate the bolus calculator.

User app 160 may be configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm, and IOB may be divided between a basal IOB and a bolus IOB, the basal IOB accounting for insulin delivered by the algorithm, and the bolus IOB accounting for any bolus deliveries.

Description of Embodiments

The primary embodiment of the invention is directed to a method for simplifying an optimization algorithm used in the calculation of quantities of a liquid drug, for example, insulin, to be periodically delivered to a user by a wearable drug delivery device 102. In the primary embodiment, rather than executing an optimization algorithm with a high computational cost, a simple stepwise exploration across all possible search spaces can be performed to bound the total computational cost and allow the calculations to be executed in embedded form.

A typical control algorithm can utilize a model of the system to be controlled to predict the outputs of the proposed drug dose. The model can be used to determine the best dose to be given to the user. For example, in an insulin delivery system, the user's glucose can be modeled as a recursive model of past glucose and insulin delivery values. Although, as would be realized by one of skill in the art, any such model can be used, one such model can be expressed by Eq. (1) as:

$$G(k)=K \cdot I(k-3)+b_1 G(k-1)+b_2 G(k-2)+b_3 G(k-3)+ \quad (1)$$

where:
k is the current cycle for which the glucose is being modelled;
K is a gain factor;
$b_1, b_2, b_3 \ldots$ are weights for each cycle of MDA 129; and
G is the estimated glucose for the current cycle, k.

The glucose model can be run recursively to predict glucose levels for future cycles. For each series of proposed insulin doses I(k+N) in the next N number of cycles, different glucose trajectory over those cycles G(k+N) can be calculated. Then, the total value of this projected insulin dose and glucose trajectory can be calculated by calculating a standard cost function, such as the exemplary cost expressed by Eq. (2) as:

$$J(k) = Q \sum_{i=1}^{N} G(k+i)^2 + R \sum_{i=1}^{n} I(k+i)^2 \quad (2)$$

where:
the left term with coefficient Q is the cost of the glucose deviations from a glucose setpoint; and
the right term with coefficient R is the cost of the insulin deviations from a particular basal rate.

Again, as would be a realized by one of skill in the art, any cost function may be used. An exemplary cost function is described in detail in U.S. patent application Ser. No. 16/789,051 (U.S. Published Patent Application No. 2021/0244881).

In certain embodiments, the glucose deviation and insulin delivery cost can be executed in various ways, such as by calculating the deviations against a specific target (such as a glucose control setpoint and basal insulin delivery) and the deviations can be calculated for various orders, such as quadratic or higher powers.

In typical applications, the calculation of the cost for each possible glucose and insulin trajectory, and determining the trajectories with a minimum cost, can be performed by optimization algorithms with high computational cost. However, as explained in the Summary above, in many medical applications, the high computational cost optimization algorithms are not necessary.

This is particularly the case in insulin delivery applications, as a typical minimum resolution of insulin pumps (e.g., 0.05 U) and variations in the timing of each dose being delivered within a short time window does not result in significant changes in the user's overall glucose outcomes.

Figure 3:
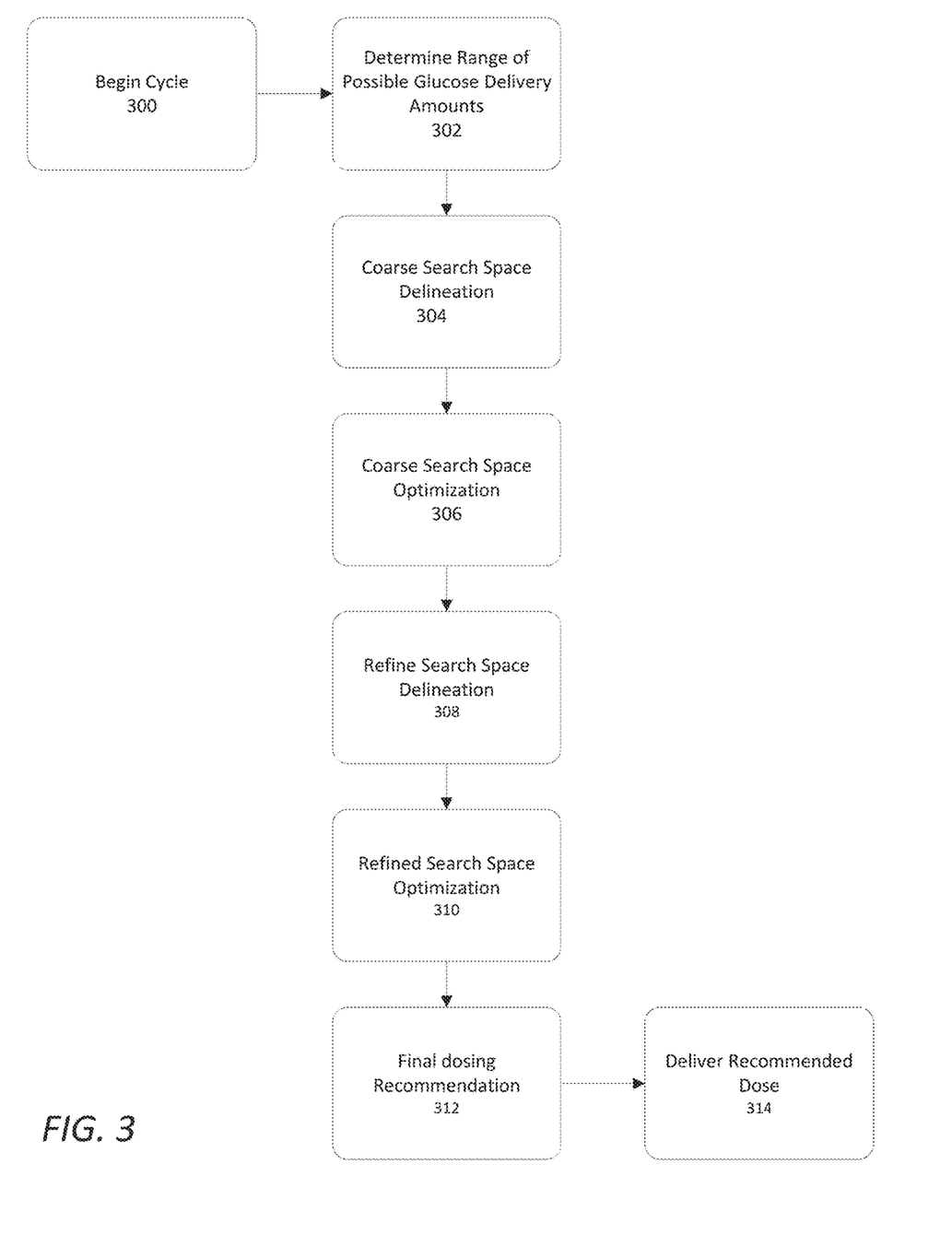
FIG. 3 is a flowchart showing the steps comprising the disclosed method.

The stepwise algorithm executed across all possible search spaces will now be explained and is shown in flowchart form in FIG. 3. In step 302 of the stepwise algorithm, the range of possible glucose delivery amounts for the current cycle is determined. Typically, the lower end of the range will be 0.0 as MDA 129 has the option, during any cycle, to cause or recommend that no dose be delivered. The upper range or limit of the possible glucose delivery amounts may be constrained by safety constraints built in the MDA 129 to prevent excess insulin from being delivered, or for any other reason. For example, in one embodiment, the delivery range can be set between 0.0 U and 0.6 U per cycle. For purposes of explanation of the disclosed method, this exemplary range will be used.

At step 304, the range is delineated into a coarse search space comprising coarse discrete quantities. For example, in the exemplary range of 0 U to 0.6 U, the search space may be delineated into 0.1 U coarse discrete quantities. Thus, the coarsely delineated search space would be delineated as: 0.0 U, 0.1 U, 0.2 U, 0.3 U, 0.4 U, 0.5 U, and 0.6 U. As would be realized by one of skill in the art, any coarse discrete quantities may be used to delineate the range, granted that they are indeed coarse relative to the minimum delivery resolution of the drug delivery device.

At step 306, the coarse search space is optimized. The search space can initially be narrowed by determining the coarse optimal insulin delivery. Specifically, all insulin delivery rates in the next N cycles can be set at a fixed value, at the coarse discrete quantities within the search space, and the corresponding glucose trajectories can be calculated.

In the explanatory example, the recursive model expressed by Eq. (1) can be calculated 7 times, each time assuming that I(k+1) . . . I(k+N) is calculated for each quantity in the coarse search space. Then, the corresponding costs can be calculated based on a cost function, an example of which is expressed by Eq. (2). In the explanatory example, this results in the following exemplary calculations:

| I(k + 1) . . . I(k + N) | 0.0 | 0.1 | 0.2 | 0.3 | 0.4 | 0.5 | 0.6 |
|---|---|---|---|---|---|---|---|
| J | 1300 | 1100 | 800 | 750 | 760 | 770 | 800 |

As can be seen, in accordance with the exemplary model and cost function, a glucose delivery of 0.3 U in the next cycle produces the lowest cost.

At step 308, the coarse delineation of the search space is refined. The search space is narrowed to a smaller area around the coarse discrete quantity with a lowest cost (in the explanatory example, 0.3 U). In the second, refined delineation of the search space, the first insulin delivery (i.e., I(k+1)) search space can be divided into finer increments, centered around the coarse discrete quantity with a lowest cost, to provide more detailed resolution of the actual insulin delivery to be provided to the user. The search space for the remaining data sets (i.e., I(k+2) ... I(k=N)) can be evaluated using the coarse discrete quantities.

In the explanatory example, the search space has been narrowed and centered around 0.3 U. Therefore, the first projected insulin delivery can be defined to be between 0.2 u and 0.4 U in a finer increment (e.g., 0.025 U) and the remaining projected insulin deliveries can be defined to be between 0.2 U and 0.4 U in a similar increment or in a coarser increment (e.g., 0.05 U), but preferably in a coarser increment to reduce computational requirements. As would be realized by one of skill in the art, the finer increment can be any desired quantity, while the range can be any range, preferably centered around the coarse solution with the minimal cost. At step 310, the refined search space can be optimized. In the explanatory example, the calculations could produce the following results:

| I(k + 1) | I(k + 2) ... I(k + N) | J |
|---|---|---|
| 0.2 | 0.2 | 800 |
| | 0.25 | 795 |
| | 0.3 | 780 |
| | 0.35 | 775 |
| | 0.4 | 770 |
| 0.225 | 0.2 | 765 |
| | 0.25 | 775 |
| | 0.3 | 760 |
| | 0.35 | 765 |
| | 0.4 | 770 |
| ... | ... | ... |
| 0.375 | 0.2 | 760 |
| | 0.25 | 756 |
| | 0.3 | 755 |
| | 0.35 | 758 |
| | 0.4 | 756 |
| 0.4 | 0.2 | 758 |
| | 0.25 | 759 |
| | 0.3 | 760 |
| | 0.35 | 762 |
| | 0.4 | 763 |

As can be seen, in the explanatory example, only 52 total calculations were required. This includes 7 calculations in the coarse search space optimization step 306 and 45 calculations in the refined search space optimization step 310 (9 [0.2, 0.225. 0.25, 0.275, 0.3, 0.325. 0.35, 0.375, 0.4]×5[0.2, 0.25, 0.3, 0.35, 0.4]). In other embodiments, wherein different intervals and ranges have been selected, the total number of calculations required in both steps 306 and 310 may change; however, the stepwise exploration of the coarse and refined search spaces is much more computationally efficient than running a conventional more computationally expensive optimization algorithm.

Finally, at step 312, the recommended insulin dose is finalized. The solution that provides a minimal cost in the second, refined search space can be provided as the recommended insulin delivery trajectory. In the explanatory example, as can be seen, the lowest calculation of the cost function occurs in the 0.375 interval, therefore, the recommended insulin delivery dose for the current cycle would be 0.375 U. At 314, the recommended dose is delivered by drug delivery device 102 to the user, as explained above.

Note that, if the recommended dose does not fall within the resolution of the drug delivery device 102, then the actual dose delivered may be rounded up or down to the nearest discrete increment that the drug delivery device 102 is capable of delivering, based on the resolution. Any remainder falling in between the incremental discrete resolutions of the drug delivery device 102 may be added to or subtracted from the recommended dose for the next cycle.

The above process is repeated for each cycle of MDA 129. In one embodiment, MDA 129 may execute a cycle every 5 minutes, although other intervals may be selected.

As previously mentioned, it is important to note that the various search spaces and resolution parameters used by the disclosed method can be widely tunable. For example, the coarse spacing calculations could be reduced to 0.2 U rather than 0.1 U resolution, as used in the explanatory example.

Overall, the disclosed method results in significantly less iterations of the calculation of the glucose model and the cost function. The 52 calculations provided in the explanatory example is significantly less calculation burdensome than a typical optimization algorithm, with a wide and multivariate search space. The resolution of the drug recommendation is still within the resolution of the drug delivery mechanism.

The following examples pertain to various embodiments of the systems and methods disclosed herein for providing a method for determining an optimal delivery of a drug by providing a stepwise exploration of a search space of possible quantities of the drug to be delivered to the user.

Example 1 is a method comprising the steps of defining a core search space, evaluating a model and cost function for each discrete quantity in the core search space, defining a refined search space, evaluating the model and cost function over the refined search space and selecting the refined discrete quantity having the lowest cost is the recommended dose of the drug.

Example 2 is an extension of Example 1, or any other example disclosed herein, base uses discrete quantities which are smaller than the discrete quantities used in the course search space.

Example 3 is an extension of Example 1, or any other example disclosed herein, wherein refined search space is smaller than the core search space.

Example 4 is an extension of Example 1, or any other example disclosed herein, wherein the range of possible doses of the drug ranges from zero to a maximum quantity determined by the medication delivery algorithm.

Example 5 is an extension of Example 4, or any other example disclosed herein, wherein the maximum quantity is dependent upon safety constraints built into the medication delivery algorithm.

Example 6 is an extension of Example 1, or any other example disclosed herein, wherein the drug is insulin delivered by a wearable drug delivery device.

Example 7 is an extension of Example 6, or any other example disclosed herein, wherein the model was a recursive glucose model used to predict glucose levels of the user in a predetermined number of future cycles based on the delivery of a particular quantity of insulin.

Example 8 is an extension of Example 7, or any other example disclosed herein, wherein the cost function calculates the cost for each possible glucose and insulin trajectory and determines a trajectory with the lowest cost.

Example 9 is an extension of Example 8, or any other example disclosed herein, wherein the cost function is based on glucose deviations and insulin deliveries wherein the glucose deviations are calculated against a specific target.

Example 10 is a system comprising a processor and software implementing a medication delivery algorithm executed by the processor, the software determining a recommended dose for drug for a current cycle of medication delivery algorithm by performing the functions of defining a core search space, evaluating a model and cost function for each discrete quantity in the core search space, defining a refined search space, evaluating the model and cost function over the refined search space and selecting the refined discrete quantity having the lowest cost is the recommended dose of the drug.

Example 11 is an extension of Example 10, or any other example disclosed herein, further comprising a drug delivery device for delivering the recommended dose of the drug to the user.

Example 12 is an extension of Example 11, or any other example disclosed herein, wherein the processor and software or integral with the drug delivery device.

Example 13 is an extension of Example 10, or any other example disclosed herein, wherein the refined discrete quantities are smaller than the course discrete quantities.

Example 14 is an extension of Example 10, or any other example disclosed herein, wherein the refined search space is smaller than the coarse search space Example 15 is an extension of Example 10, or any other example disclosed herein, wherein the range of possible doses of the drug ranges from zero to a maximum quantity determined by the medication delivery algorithm.

Example 16 is extension of Example 15, or any other example disclosed herein, wherein the maximum quantity is dependent upon safety constraints built into the medication delivery algorithm.

Example 17 is an extension of Example 11, or any other example disclosed herein, wherein the drug is insulin delivered by the wearable drug delivery device.

Example 18 is an extension of Example 17, or any other example disclosed herein, wherein the model is a recursive glucose model used to predict glucose levels of the user in a predetermined number of future cycles based on delivery of a particular quantity of insulin.

Example 19 is an extension of example 18, or any other example disclosed herein, wherein the cost function calculates the cost for each possible glucose and insulin trajectory and determines a trajectory with a lowest cost.

Example 20 is an extension of Example 19, or any other example disclosed herein, wherein the cost function is based on glucose deviations and insulin delivery deviations, wherein the glucose deviations are calculated against the specific target.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

To those skilled in the art to which the invention relates, many modifications and adaptations of the invention may be realized. Implementations provided herein, including values of tunable parameters, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A method comprising:
   determining a search space of possible drug delivery amounts for a current cycle of medication delivery in an automated drug delivery system;
   separating the search space into ranges of solutions;
   narrowing the search space by determining a selected range in the range of solutions that minimizes a cost function;
   separating the selected range into a list of refined values for a first delivery of the drug, the list of refined values being separated by a first fine increment;
   evaluating a set of subsequent deliveries of the drug following the first deliveries of the drug in the list of refined values, the set of subsequent deliveries being separated by a second coarse increment; and
   selecting a solution based on the set of subsequent deliveries that minimizes the cost function.

2. The method of claim 1, wherein the first fine increment is smaller than the second coarse increment.

3. The method of claim 1, wherein separating the search space into ranges of solutions is performed using a third coarse increment.

4. The method of claim 1, wherein the search space of possible drug delivery amounts ranges from zero to a maximum quantity according to one or more safety constraints.

5. The method of claim 1, wherein the drug is insulin and the automated drug delivery system is a part of a wearable drug delivery device.

6. The method of claim 1, wherein determining the selected range comprises evaluating a recursive glucose model configured to predict glucose levels of a user of the automated drug delivery system in a predetermined number of future cycles based on delivery of a particular quantity of insulin.

7. The method of claim 6, wherein the cost function calculates the cost for each possible glucose and insulin trajectory and determines the trajectory with a lowest cost.

8. A non-transitory computer-readable medium storing instructions configured to cause a processor to:
   determine a search space of possible drug delivery amounts for a current cycle of medication delivery in an automated drug delivery system;
   separate the search space into ranges of solutions;
   narrow the search space by determining a selected range in the range of solutions that minimizes a cost function;
   separate the selected range into a list of refined values for a first delivery of the drug, the list of refined values being separated by a first fine increment;
   evaluate a set of subsequent deliveries of the drug following the first deliveries of the drug in the list of refined values, the set of subsequent deliveries being separated by a second coarse increment; and
   select a solution based on the set of subsequent deliveries that minimizes the cost function.

9. The medium of claim 8, wherein the first fine increment is smaller than the second coarse increment.

10. The medium of claim 8, wherein separating the search space into ranges of solutions is performed using a third coarse increment.

11. The medium of claim 8, wherein the search space of possible drug delivery amounts ranges from zero to a maximum quantity according to one or more safety constraints.

12. The medium of claim 8, wherein the drug is insulin and the automated drug delivery system is a part of a wearable drug delivery device.

13. The medium of claim 8, wherein determining the selected range comprises evaluating a recursive glucose model configured to predict glucose levels of a user of the automated drug delivery system in a predetermined number of future cycles based on delivery of a particular quantity of insulin.

14. The medium of claim 8, wherein the cost function calculates the cost for each possible glucose and insulin trajectory and determines the trajectory with a lowest cost.

15. An automated drug delivery system comprising:
a reservoir configured to store a drug;
a drug delivery device configured to dispense the drug to a user;
a processor; and
a non-transitory computer-readable medium storing instructions configured to cause the processor to:
determine a search space of possible drug delivery amounts for a current cycle of medication delivery;
separate the search space into ranges of solutions;
narrow the search space by determining a selected range in the range of solutions that minimizes a cost function;
separate the selected range into a list of refined values for a first delivery of the drug, the list of refined values being separated by a first fine increment;
evaluate a set of subsequent deliveries of the drug following the first deliveries of the drug in the list of refined values, the set of subsequent deliveries being separated by a second coarse increment; and
select a solution based on the set of subsequent deliveries that minimizes the cost function.

16. The system of claim 15, wherein the first fine increment is smaller than the second coarse increment.

17. The system of claim 15, wherein separating the search space into ranges of solutions is performed using a third coarse increment.

18. The system of claim 15, wherein the search space of possible drug delivery amounts ranges from zero to a maximum quantity according to one or more safety constraints.

19. The system of claim 15, wherein the drug is insulin and the automated drug delivery system is a part of a wearable drug delivery device.

20. The system of claim 15, wherein determining the selected range comprises evaluating a recursive glucose model configured to predict glucose levels of the user in a predetermined number of future cycles based on delivery of a particular quantity of insulin.

* * * * *